United States Patent [19]

Shartle et al.

[11] Patent Number: 5,230,866

[45] Date of Patent: Jul. 27, 1993

[54] CAPILLARY STOP-FLOW JUNCTION HAVING IMPROVED STABILITY AGAINST ACCIDENTAL FLUID FLOW

[75] Inventors: Robert Shartle, Livermore; Donald Besemer, Los Altos Hills; Michael Gorin, Los Altos, all of Calif.

[73] Assignee: Biotrack, Inc., Mountain View, Calif.

[21] Appl. No.: 663,217

[22] Filed: Mar. 1, 1991

[51] Int. Cl.$^5$ .................. B01L 11/00; G01N 21/00
[52] U.S. Cl. .................. 422/103; 422/68.1; 422/81; 422/82; 422/100; 435/301; 436/45; 436/179; 436/180
[58] Field of Search ........... 422/100, 102, 103, 68.1, 422/81, 82; 436/45, 179, 180; 435/810, 301; 73/864.71, 865.71; 383/45, 100, 103

[56] References Cited

U.S. PATENT DOCUMENTS

| | | | |
|---|---|---|---|
| 4,260,687 | 4/1981 | Jacobson et al. | 435/301 |
| 4,318,994 | 3/1982 | Meyer et al. | 435/301 |
| 4,426,451 | 1/1984 | Columbus | 436/518 |
| 4,503,012 | 3/1985 | Starr | 422/100 |
| 4,624,928 | 11/1986 | Qureshi | 436/179 |
| 4,718,778 | 1/1988 | Ichikawa | 383/100 |
| 4,868,129 | 9/1989 | Gibbons et al. | 436/179 |
| 4,876,203 | 10/1989 | Guigan et al. | 436/45 |
| 4,883,763 | 11/1989 | Holen et al. | 436/45 |
| 4,898,832 | 1/1991 | Klose et al. | 436/45 |
| 4,999,304 | 3/1991 | Robertson et al. | 436/45 |
| 5,104,813 | 4/1992 | Besemer et al. | 436/179 |

Primary Examiner—Robert J. Warden
Assistant Examiner—Christopher Y. Kim
Attorney, Agent, or Firm—Cooley Godward Castro Huddleson & Tatum

[57] ABSTRACT

A capillary stop-flow junction located in a housing at an end of a capillary passageway used to transport a liquid and at the beginning of a non-capillary internal chamber in the housing, in which the stop-flow junction contains an improvement which comprises 1) means for selectively trapping a gas in the capillary passageway and non-capillary chamber, wherein when the means for trapping is activated and the liquid enters the capillary passageway, the gas is compressed by the liquid as the liquid flows through the capillary channel and stops flowing at the stop-flow junction; or 2) a stop-flow nozzle surrounding the capillary passageway and projecting into the chamber; or 3) the stop-flow junction being formed from a single housing body member; or 4) a rupture junction in the capillary pathway, wherein the rupture junction is a stop-flow junction providing less maximum available back pressure than the capillary stop-flow junction. Diluters capable of serial dilution that use the stop-flow junctions of the invention are also described.

10 Claims, 6 Drawing Sheets

CAPILLARY STOP-FLOW JUNCTION HAVING IMPROVED STABILITY AGAINST ACCIDENTAL FLUID FLOW

INTRODUCTION

1. Technical Field

This invention relates to methods and apparatuses used for controlled transport of liquids by capillary action and gravity, particularly the automatic measuring and diluting of small volumes of liquids using cartridges in which flow of sample and diluent is controlled at a junction between capillary-flow and non-capillary-flow regions referred to herein as a stop-flow junction.

2. Background

The phrase "stop-flow junction" was introduced to describe a control region in a capillary passageway that is used in a number of prior inventions arising out of the laboratories of the present invention. A stop-flow junction is a region in a fluid track that marks the junction between an early part of the fluid track in which sample flows by capillary action (and optionally gravity) and a later part of the fluid track into which sample does not normally flow until flow is initiated by some outside force, such as an action of the user.

A stop-flow junction is not a traditional valve as it has no moving parts. Rather, this junction relies on back pressure from the surface tension of the liquid sample to stop flow. This back pressure can be created in a number of ways. For example, back pressure is created when the cross-sectional area of a liquid flowpath increases in a region in which there is contact between the liquid and the container walls (e.g., when a small tube enters a larger chamber or when the cross-sectional area of a channel increases). More consistent operation of a stop-flow junction is achieved when the increase in cross-sectional area of the flowpath is abrupt rather than gradual, particularly when there is a break in capillarity in the sample flowpath. In many cases, the junction will be formed when a small-diameter capillary channel enters a larger, non-capillary chamber. A small channel or tube can enter the larger chamber at a right angle or at an angle other than a right angle. The angle between the internal wall of the small tube and the surface of the chamber in the latter case will be different at different locations around the circumference of the junction.

In general, for small (capillary-size) junctions, the back pressure will be largely determined by the smallest radius of curvature assumed by the meniscus. For example, when a capillary tube with a circular crosssection enters a larger space so that liquid bulges out into the space under hydrostatic pressure, the meniscus will be approximately spherical, and the back pressure ($\delta p$) is given by the Young-Laplace equation: $\delta p = 2\gamma/R$, were $\gamma$ is the surface tension of the sample fluid and R is the radius of curvature. See, Miller and Neogi, "Interfacial Phenomena: Equilibrium and Dynamic Effects", Marcel Dekker, Inc., New York, 1985, and Davies and Riedeal "Interfacial Phenomena", 2nd Ed., Academic Press, New York, 1963. If the fluid meets the surface at an angle greater than 0°, this back pressure will be reduced by a geometric term. The radius, R, will change (become smaller) as the hydrostatic pressure increases, so that the back pressure and hydrostatic pressure balance. As hydrostatic pressure increases, R reaches a minimum value (maximum curvature) determined by the geometry of the device and the contact angle. The corresponding back pressure defines the maximum hydrostatic pressure sustainable by the stop-flow junction.

Back pressure is also created when the surface that the liquid contacts changes to decrease adhesion between the liquid and the container wall (for example, when an aqueous sample moves from a hydrophilic to a hydrophobic surface). The surface properties of the various interior surfaces of the device of the invention can and generally will be controlled by various physical and/or chemical treatments. For a discussion of controlling surface properties of similar devices, see commonly assigned U.S. application Ser. No. 880,793, filed Jul. 1, 1986. For example, plastic surfaces can be treated to increase their hydrophilicity. Either the whole apparatus or specific parts can be treated. Alternatively, different parts of the apparatus can be made of different plastics. For capillary flow, contact angles of less than 90° are sufficient, preferably 10°–85° and most preferably 30°–60°. In order to provide these contact angles for aqueous samples, the capillary surfaces will be hydrophilic (at least to some measurable extent). For non-aqueous liquids, a hydrophobic surface would be appropriate. By using a combination of container wall geometry and surface wetability, a back pressure range of from 0 (no change in cross-sectional area or surface adhesion) to 20 cm $H_2O$ and higher can easily be achieved with water as the liquid. When the back pressure is 0, the location in question is not a stop-flow junction. A stop-flow junction occurs when there is sufficient back pressure to prevent the flow of sample past a particular point in the flowpath; e.g., from the measuring chamber to the receiving chamber of a dilution apparatus as described herein.

When considering the amount of available back pressure for any given design, the realities of manufacturing and of the physical world at the microscopic level must be considered. Imperfections in the container walls during gradual widening of chambers may cause liquid to "creep" more on one side than another, thereby allowing the stop-flow junction to fail. Liquid can also creep around corners when imperfections are present that result in unbalanced forces. Unbalanced forces will also be present when the junction is not horizontal. A horizontal junction, for example, occurs when a vertical tube enters the top horizontal surface of a chamber. If a horizontal tube enters a vertical wall of a container, a vertical junction is present, and the pressure at the bottom of the stop-flow junction will be greater than the pressure at the top of the junction, due to hydrostatic pressure caused by the different heights of liquid. Nonetheless, non-horizontal stop-flow junctions can be created by reducing the diameter of the smaller channel containing liquid as it enters the larger area, thereby reducing the difference in pressure between the upper and lower portions of the junction, and other manufacturing imperfections can be alleviated by quality control operations, although with increased costs of manufacturing.

U.S. Pat. No. 4,426,451, which was developed in other laboratories, describes a number of regions that it refers to as "meniscus control means" for use in a device in which there is capillary flow from one capillary zone to another. The meniscus control means described in that patent can be used in apparatuses in which capillary/capillary transactions and temporary stoppage of flow is desired before flow continues into the next zone.

However, the patent is not directed to stopping flow when the second zone is not a capillary zone. In contrast to the specific teachings of the '451 patent, which indicate that the walls of the capillary chamber must gradually narrow and gradually expand in order to provide for flow stop, an abrupt widening has been found to be more effective in the practice of the present invention when the second chamber is not a capillary space. Although it is recognized that imperfections will exist on the molecular level, it is preferred that the junction be as sharp as possible from a macroscopic view point, approaching as closely as possible the ideal junction formed by the intersection of the surface (which can be curved) forming the walls of the measuring chamber with the surface forming the wall of the receiving chamber surface in which the stop-flow junction is found (which can also be curved). Maintaining a horizontal junction to avoid pressure differentials, reducing the area of the junction, changing the surface of the capillary so as to decrease the hydrophilic character (for aqueous solutions), providing smooth surfaces (rough surfaces encourage creep of liquid along the surface), and providing an abrupt change in cross-sectional area (preferably providing an angle between intersecting surfaces of about 90° or lower) all operate to prevent creep of liquid from one chamber to the other.

It should be recognized that flow stop can occur both stably and metastably. A metastable flow stop is one in which flow stops on the macroscopic level but may resume without apparent cause after a time interval of a few seconds to a few minutes. Gradual creep of liquids along container walls or through microscopic or submicroscopic channels resulting from imperfections in the manufacturing process is believed to be the mechanism by which flow starts again once it has stopped. Additionally, vibrations (such as might be caused by persons walking near the apparatus or starting and stopping of nearby equipment, such as air-conditioning units) may also be sufficient to start flow in a metastable situation. However, there is no requirement of absolute stability in cases where an apparatus is designed for addition of a diluent and eventual starting of flow at the stop-flow junction. Accordingly, any flow stop which can be sustained for at least 10 seconds, preferably at least one minute, and more preferably at least five minutes, is sufficient for use in a diluter.

Although these prior stop-flow junctions were sufficient for most uses, improvements in stability of the stop-flow junction against accidental start has been desirable from the point of view of developing a commercial apparatus. A number of factors contribute to the instability of the junction. For example, variations in the sample physical properties (such as density, viscosity, hematocrit, microheterogeneity, surface tension, and contact angle with housing walls) can affect both the forward pressure acting to favor flow and the back pressure available at the stop-flow junction to stop flow. Density controls the hydrostatic pressure at the junction. Surface tension and contact angle determine the pressure that the junction can exert in opposition to flow. Viscosity determines the rate at which the sample moves to the junction and therefore the excess back pressure (over that necessary for an equilibrium state) required to prevent the momentum of the sample from breaking through the junction. Hematocrit of blood sample affects both viscosity and density. Microheterogeneity has an impact on local properties at the junction, which can vary significantly from the bulk properties of the sample. Other variations include sample volume, which affects hydrostatic pressure by varying the height of the upper sample surface above the junction; method of sample application by different uses (or the same user at different times); variations from lot to lot of the physical properties, such as contact angle with a standard liquid, of the housing out of which the diluter is made; variations in the size and shape of the junction arising during manufacturing, such as can be caused by plastic "burrs" at corners and edges; and local external factors, such as mechanical vibrations caused by nearby machinery or foot travel, as well as variations in orientation of the diluter from a horizontal operating position.

While it is possible for any of the previous diluters arising out of the inventors' laboratory to be used despite these potential problems, such as by designing a monitor in which the diluter will be used that is capable of detecting when flow accidentally starts prior to the desired time, improvement of the reliability of operation is highly desirable. For example, few patients desire having a second finger puncture for the purpose of obtaining a second blood sample. In other cases, the patient may have left and no more sample may be available, thereby inconveniencing both the patient and the physician. Thus, there remains a need for improved stop-flow junctions having increased stability against accidental fluid flow and for diluters that incorporate these improved features.

RELEVANT LITERATURE

West German published patent application DE3328964C1, publication date Feb. 14, 1985, describes a device for the automatic, discontinuous sampling of fluids using a capillary tube that acts as a measuring device and which can be either dipped into a fluid being sampled or alternatively moved into a position from which the sample is transported with a diluent to an analyzer by a pump or suction. U.S. Pat. No. 4,454,235 describes a capillary tube holder for liquid transfer in immunoassays. U.S. Pat. No. 4,233,029 describes a liquid transport device formed by opposed surfaces spaced apart a distance effective to provide capillary flow of liquid without providing any means to control the rate of capillary flow. U.S. Pat. Nos. 4,618,476 and 4,233,029 describe a similar capillary transport device having speed and meniscus control means. U.S. Pat. No. 4,426,451 describes another similar capillary transport device including means for stopping flow between two zones, flow being resumed by the application of an externally-generated pressure. U.S. Pat. Nos. 3,811,326; 3,992,150; 4,537,747; and 4,596,780 describe various processes and devices in which a capillary tube is used to take up a predetermined volume of the test solution and the charged capillary is then placed in a cuvette or other container of liquid that is used as reagent or diluent. U.S. Pat. No. 3,799,742 describes an apparatus in which a change in surface character from hydrophilic to thereby metering the sample present. U.S. Pat. No. 5,077,017 and U.S. Pat. No. 4,868,129, both of which are assigned to the same assignee as the present application, described a number of dilution and mixing cartridges.

SUMMARY OF THE INVENTION

The present invention provides an improved stop-flow junction for use in, among other potential locations, a self-contained dilution apparatus that does not require the use of externally generated force (except gravity) to move liquids between its various parts or to provide for reproducible dilution of samples. The principal motive force in such devices arises from capillarity and gravity (resulting in hydrostatic pressure), thus giving rise to the name stop-flow junction, since a stop-flow junction occurs at the junction of a capillary region and a region where flow does not occur solely as a result of capillarity and gravity.

Stop-flow junctions are described herein that provide increased stability in the "stop" state. A series of individual improvements are available in accordance with the present invention, or all of the improvement can be present in the same device. Specifically, the device of the invention comprises a capillary stop-flow junction located in a housing at an end of a capillary passageway for transporting a liquid and at the beginning of a non-capillary chamber, in which an improvement is present which comprises:

a. means for selectively trapping a gas in said capillary passageway and non-capillary chamber, wherein when said means for trapping is activated and said liquid enters said capillary passageway, said gas is compressed by said liquid as said liquid flows through said capillary channel and stops flowing at said stop-flow junction; or
b. a stop-flow nozzle surrounding said capillary passageway and projecting into said chamber;
c. a stop-flow junction formed from a single housing body member; or
d. a rupture junction in said capillary pathway, wherein said rupture junction is a stop-flow junction providing less back pressure than said capillary stop-flow junction.

One, some, or all of these improvements can be present in a single stop-flow junction of the invention.

The improved stop-flow junctions of the invention can be used in a diluter that, in addition to containing the improved stop-flow junctions, also provides other advantages because of its improved design, such as improvement in reproducibility of sample measurement and dilution control. The improved diluter is an apparatus for automatically carrying out a dilution of an aqueous sample with one or more aqueous diluents in a housing, comprising in said housing:

(1) a sample application site for receiving a sample;
(2) a rupture chamber comprising a vented interior chamber;
(3) a mixing chamber comprising a vented interior chamber having a first volume;
(4) a diluent application site for receiving a diluent;
(5) capillary flow means comprising:
  (a) a central valved segment having a first and a second end;
  (b) a valve located in said central valved segment;
  (c) a sample segment connecting said sample application site to said first end of said central valved segment;
  (d) a rupture segment connecting said rupture chamber to said first end of said central valved segment; and
  (e) a measuring segment connected to said second end of said central valved segment and having first and second exits, wherein said first exit connects said measuring segment to said mixing chamber and wherein said measuring segment has a second volume smaller than said first volume of said mixing chamber;
  (f) a first stop-flow junction located at said first exit of said measuring segment and adapted to the surface-tension characteristics of the sample so as to provide sufficient back pressure resulting from contact between the sample and wall means of said housing at said first stop-flow junction to prevent sample from flowing through said first stop-flow junction in the absence of diluent;
  (g) a second-stop flow junction located at said second exit of said measuring segment and adapted to the surface-tension characteristics of the sample so as to provide sufficient back pressure resulting from contact between the sample and wall means of said housing at said second stop flow junction to prevent sample from flowing through said second stop-flow junction in the absence of diluent; and
  (h) a third stop-flow junction located at the junction of said rupture segment and said rupture chamber and adapted to the surface-tension characteristics of the sample so as to provide sufficient back pressure resulting from contact between said sample and wall means of said housing at said third stop flow junction to prevent sample from flowing through said third stop-flow junction in the absence of diluent, wherein said third stop-flow junction provides less maximum-available back pressure than said first stop-flow junction;

whereby addition of sample to said sample application site causes sample to fill said capillary flow means; and (6) diluent flow means connecting said diluent application site to said second exit of said measuring segment.

BRIEF DESCRIPTION OF THE DRAWINGS

The present invention will be better understood by reference to the following detailed description of the invention when considered in conjunction with the attached drawings that form a part of the present specification, wherein.

DESCRIPTION OF THE SPECIFIC EMBODIMENTS

I. New stop-flow junction

A. General background

Figure 1:
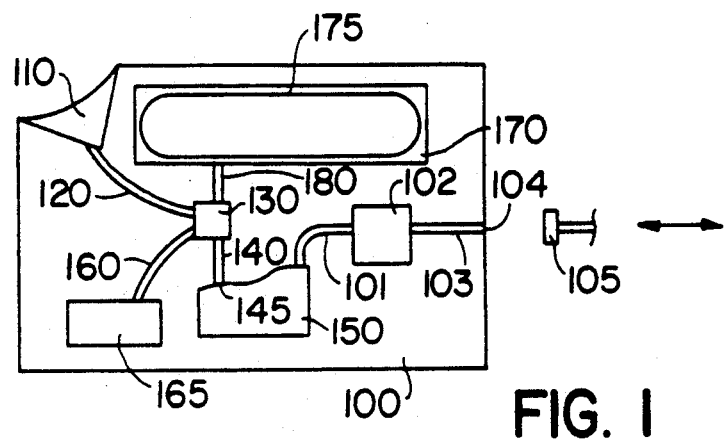
FIG. 1 is a vertical cross-section of a first embodiment of the invention showing a vent-assisted stop-flow junction.

The present invention provides an improved stop-flow junction for use in apparatuses that require stoppage of capillary flow followed by controlled restart of flow. Such stop-flow junctions are particularly useful in apparatuses and methods in which small samples are automatically measured and diluted. Such apparatuses are generally small, convenient to use, and require no moving parts for the movement of fluid, with gravity and capillary action being sufficient to provide all fluid motive forces required for the sample measurement and dilution steps. Such dilution and mixing cartridges are described in U.S. Pat. No. 4,868,129, U.S. Pat. No. 5,077,017, and U.S. Pat. No. 5,104,813. However, the apparatuses of the present invention provide a number of improvements in stop-flow junctions relative to those described in previous dilution and mixing apparatuses, particularly in ease of manufacture and reliability of operation for large numbers of diluters made from the same mold. Among the specific improvement of the present apparatus are (1) means for selectively trapping a gas in a capillary passageway and non-capillary chamber adjacent to a stop-flow junction, wherein when said means for trapping is activated and a liquid enters said capillary passageway, said gas is compressed by said liquid as said liquid flows through said capillary channel and stops flowing at said stop-flow junction; (2) a stop-flow nozzle surrounding a capillary passageway and projecting into a chamber, with the stop-flow junction being at the entrance of the capillary passageway into the chamber; (3) a stop-flow junction formed from a single housing body member; and (4) a rupture junction in a capillary pathway, wherein said rupture junction is a stop-flow junction providing less maximum available back pressure than said capillary stop-flow junction. Each of these improvements, which can occur alone or in combination with any other of these improvements, is discussed in detail below.

The basic features of a stop-flow junction are described in the patents and patent applications identified above in the background section of this application. There are two required parts to a stop-flow junction, the first of which is a region in a fluid pathway in which fluid flow occurs either solely under the influence of capillary action or under the combined influence of capillary action and gravity. The junction exists at the end of this region of free flow at a transition to a region at which capillary flow will cease, even in the presence of a gravitationally derived pressure arising from a liquid head above the capillary-stop junction. Well-known examples of capillary junctions exist in familiar devices, such as a capillary tube used for obtaining blood samples from a finger puncture. In such a simple device, the stop-flow junction is the end of the capillary tube, since capillary forces retain sample inside the tube, even when the tube is oriented vertically and gravitational forces are present on the sample. Other examples are described in the previously discussed publications and patent applications.

B. Vent-assisted stop-flow junction

The first of the improvements that have been recognized and developed by the current inventors is a technique (and associated apparatuses) in which a gas (usually air from the atmosphere surrounding the apparatus in which the stop-flow junction is located) is trapped and compressed when a liquid enters the capillary portion of the passageway and flows through the passageway to the stop-flow junction. The trapping must be selective since the trapped gas will need to be vented in order for flow to continue unimpeded to other parts of the apparatus at an appropriate time. By properly selecting sizes of the compressed air space relative to the gravitational and capillary forces present in the device, reliability of flow stoppage at the stop-flow junction can be increased many fold over. Since the volume of the trapped gas is manipulated most easily by changing the size of the vent channels and chambers, this aspect is referred to as a vent-assisted stop-flow junction.

The operation of a vent-assisted capillary stop-flow junction is readily understood by reference to FIG. 1 and the mode of operation of the apparatus shown in the figure. However, it should be recognized that this is not the sole embodiment by which the present invention can operate and that the embodiment shown in FIG. 1 is merely exemplary of this aspect of the invention.

FIG. 1 is a vertical, cross-sectional schematic drawing of a dilution apparatus having a vent-assisted stop-flow junction. The diluter shown in FIG. 1 is similar to the single-dilution apparatus described in U.S. Pat. No. 4,868,129 with the additional flow directing chamber of U.S. Pat. No. 5,104,813. Reference may be made to this earlier patent and patent application for detail on the various parts of the apparatus. The present discussion will address the vent-assisted stop-flow junction without prolonged discussion of other aspects of the device.

Cartridge 100 contains a sample application site 110, a capillary channel 120 leading from sample application site 110 to flow directing chamber 130, capillary measuring chamber 140, mixing chamber 150, capillary passageway 160 leading from flow directing chamber 130 to waste chamber 165, a rupturable container 175 of diluent in an internal chamber functioning as a diluent application site 170, and a channel 180 leading from the diluent application site to the flow directing chamber 130. All of these parts of the apparatus have been previously described in earlier patents and patent applications. Parts of the device relating specifically to the vent-assisted feature include an initial capillary channel 101 leading to a relatively large interior chamber 102 referred to as a vent-surge chamber, capillary channel 103 connecting vent-surge chamber 102 to the environment surrounding cartridge 100, where vent opening 104 exists to allow atmospheric gases to enter and leave venting channel 103 and other interior chambers of the device, and vent closure 105, which is capable of being moved in the directions shown by the arrow to alternatively close and open the vent at 104.

The operation of the vent-assisted stop-flow junction can readily be seen from the following description and by reference to FIG. 1. Prior to application of a sample to sample application site 110, vent closure 105 is moved to the left where it seals against the housing at vent 104. The vent closure substantially seals the vent from the external environment. Any means that accomplishes this result is satisfactory, such as providing a flexible pad that presses against the surface of the housing at vent exit 104; providing a close-fitting, smooth disc that contacts a corresponding smooth surface on the housing; or any other effective means of sealing off the internal space in the housing from the surrounding atmosphere. The vent closure is typically operated by a monitor into which the housing has been inserted.

After the vent is closed, sample is applied at sample application site 110. Sample flows through capillary 120 to flow directing chamber 130 and then into measuring chamber 140. When sample first enters measuring chamber 140, it creates a sealed interior space consisting of measuring chamber 140, mixing chamber 150, and any venting spaces. In the embodiment shown in FIG. 1, the venting spaces consist of capillary channels 101 and 103 and vent-surge tank 102. However, this vent-surge tank is included merely to provide an appropriate volume for the trapped air or other gas present in the indicated chambers and is therefore optional. If measuring chamber 140, mixing chamber 150, and the vent spaces leading to vent exit 104 provide the desired compressible volume of air, no vent-surge chamber 102 is required. As sample flows down capillary measuring chamber 140, the air trapped in the enclosed space is compressed. This compressed air will act to oppose the forward motion of the liquid in the measuring chamber and thus act to stabilize stop-flow junction 145 at the intersection of measuring chamber 140 and mixing chamber 150.

Earlier applications from the laboratories of the present inventors have described vent closures that were designed to stop flow of sample in capillary passageways without requiring the concurrent presence of a stop-flow junction. Such vent closures were different from those used in the present invention. The build-up of pressure in the enclosed space in the present invention is only sufficient to impede and partially counteract forward-directed pressure from the weight of the sample. If no stop-flow junction is present at a location where flow stoppage is desired and a vent closure is used in the manner described herein, forward-directed pressure would cause sample to continue to flow beyond the desired location.

Figure 6:
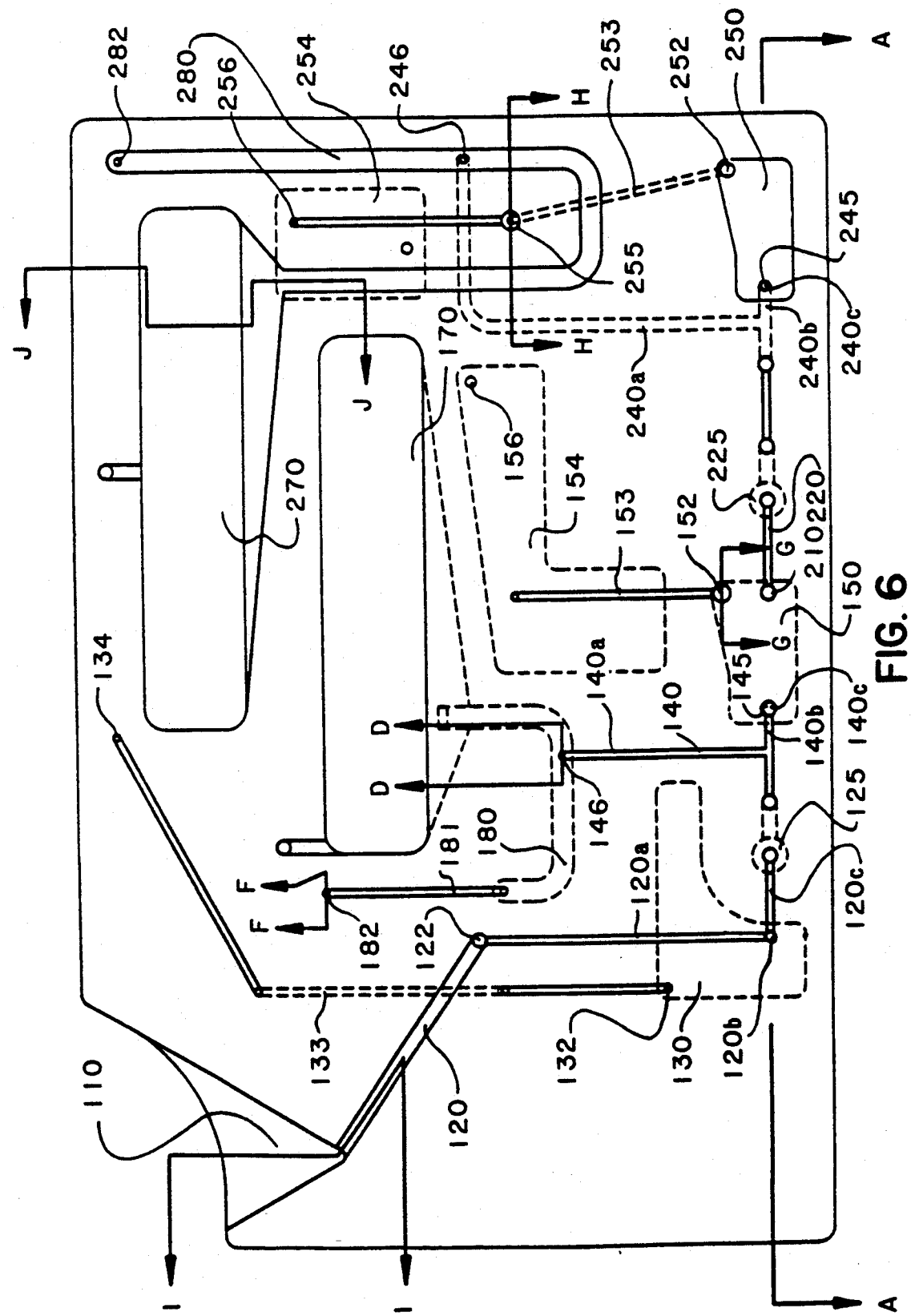
FIG. 6 is a vertical cross-section of a diluter of the invention showing a stop-flow junction having the principal features of the stop-flow junction embodiments of FIGS. 1, 2, 4, and 5 along with other features of the diluter as a whole.

Since stop-flow junction 145 is designed so that flow will occur at this location during the dilution step, maximum capillary force available at this junction is designed to be weaker then the head pressure at the stop junction for all cases in which diluent is present and vent 104 is open. This can be achieved simply by selecting an appropriate size for the opening at stop-flow junction 145. When the opening at stop-flow junction 145 is circular, Formula 1 below allows design of an appropriate junction for any given sample and housing type merely by selecting an appropriate radius for the opening.

$$dgh_1 > \frac{2\gamma\cos\theta}{r} \quad \text{Formula 1}$$

wherein:
d = density of sample
g = gravitational constant
$h_1$ = head on stop-flow junction (sample and diluent)
$\gamma$ = surface tension of sample
$\theta$ = contact angle of sample on housing wall
r = radius of opening at stop-flow junction It will be recognized that Formula 1 above is intended for circular openings used as stop-flow junctions and that other shapes will require the use of different formulas. Other parameters that can be used to control flow are also evident from the formula. For example, the head height available can be adjusted by appropriate design of the cartridge (e.g., a tall thin measuring chamber to maximize head height, or low-lying broad measuring chamber to minimize height). The contact angle can likewise be used to control back pressure, either by selecting a material for manufacture of the housing (either the entire housing or a part thereof) that provides the appropriate contact angle or by modifying the surface properties of the housing at an appropriate location, e.g., by plasma etching, as has been described in earlier patents, such as U.S. Pat. No. 4,756,884. Empirical adjustment of head height and surface characteristic by appropriate design of the cartridge can be used to control back pressure at a stop-flow junctions of any shape.

the maximum flow-opposing pressure created by compression of air in the internal spaces of the diluter when vent 104 is closed and a sample is applied should be equal to or less than the head pressure on the stop-flow junction. Equal internal pressure to balance the head pressure is preferred. This opposing pressure can be varied by varying the ratio of the pre-compressed and compressed volumes of air. In order to allow flexibility of design, vent-surge tank 102 can be provided in different volumes, since this part of the apparatus does not affect the dilution that occurs in mixing chamber 150 (an additional stop-flow junction can be included in the early portion of the vent leading to the surge tank to keep the mixture from entering the surge tank). The volume of the surge chamber is selected so that the pre-compression and post-compression trapped-gas volumes are sufficient to satisfy the inequality set forth below in Formula 2 below:

$$dgh_2 \geq P\left(\frac{V_1}{V_2} - 1\right) \quad \text{Formula 2}$$

wherein:
d = density of sample
g = gravitational constant
$h_2$ = head on stop-flow junction (sample alone)
P = atmospheric pressure
$V_1$ = pre-compression trapped-gas volume
$V_2$ = post-compression trapped-gas volume In the embodiment shown in FIG. 1, $V_2$ is the sum of the volume of the mixing chamber and the volume of the total vent space including the surge chamber. $V_1$ is $V_2$ plus the volume of the measuring chamber. Other configurations will result in compressions occurring in different parts of the apparatus, as shown in FIG. 6 below for a different embodiment.

In some embodiments of the invention, the formulas described above will not strictly apply. For example, even in the embodiment shown in FIG. 1, a different mode of operation can allow proper functioning of a vent-assisted stop-flow junction without the indicated formulas being strictly adhered to. For example, in Formula 1, the momentum of diluent flowing from diluent application site 170 can be used to overcome back pressure at the stop-flow junction even if the height of diluent and sample together are insufficient to start flow from an equilibrium state. Alternatively, the various techniques described in U.S. Pat. No. 4,868,129 can be used to start flow rather than relying on the increased height of the column of sample and diluent. Other factors (such as controlling capillary action by varying the surface attraction of housing walls to liquid sample) can also be used in designing properly sized and shaped channels. However, use of these formulas in producing an initial design, followed by emperical optimization is preferred over attempts to calculate a design from physical principles.

Essential characteristics of this aspect of the invention, however, are that compression of trapped gas that would otherwise escape through a vent takes place in an enclosed space created by closing all vents to that space and that the advancing liquid supplies the compressive force), with the resulting increase in internal gas pressure being used to oppose the flow of sample past the stop-flow junction under consideration. The increase in internal pressure is not itself sufficient to stop flow in the absence of a stop-flow junction at the location where stoppage of flow is desired. It should be noted that an internal gas pressure equal or even slightly greater than the head pressure, while sufficient to maintain an equilibrium state once flow is stopped, is not necessarily sufficient by itself to stop flow of a moving liquid (because of forward-base capillary action and momentum) in the absence of the back pressure created at the stop-flow junction.

C. Stop-flow junction nozzle

An additional feature that can be used to increase stability of the stop-flow junction is to provide a nozzle surrounding the capillary portion of the stop-flow junction that projects into the non-capillary region (which can include projection into a recessed area in a chamber wall). The nozzle is shaped so as to provide exterior nozzle surfaces which form an acute angle with the adjacent surfaces of the interior wall of the capillary passageway. A typical projection with acute angles to prevent creep of liquids around the edges of the stop-flow junction and to increase the practical amount of available back pressure is shown in FIG. 2.

Figure 2:
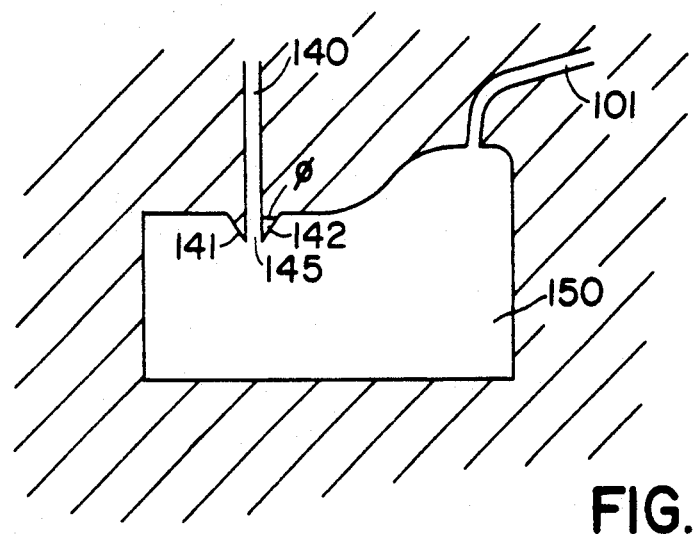
FIG. 2 is a vertical cross-section of a second embodiment of the invention showing a stop-flow nozzle.

FIG. 2 is an expanded cross-section of the area surrounding stop-flow junction 145 shown in FIG. 1. Measuring chamber 140 is visible along with the stop-flow junction 145 at the point where capillary chamber 140 enters non-capillary mixing chamber 150. Housing walls 141 surrounding the opening at 145 project into chamber 150. Surface 142 of the wall forms an acute angle (represented by $\phi$) with the adjacent interior wall of measuring chamber 140. The preferred shape for the nozzle formed by walls 141 is a cone when stop-flow junction 145 is circular. However, there are no particular limitations on the shape of the nozzle as long as an acute angle is maintained. A cone recessed into a surface of a non-capillary chamber is preferred, as shown in FIGS. 7B–7D below, when liquid flow or other motion (such as of a mixing element) occurs in a chamber containing a stop-flow junction.

D. Through-body stop-flow junction

Still further improvements in stability of the stop-flow junction can be achieved by forming the stop-flow junction from a single housing body member rather than forming it at the junction of two members used to form a cavity. Such stop-flow junctions are referred to as through-body stop-flow junctions.

Figure 3A:
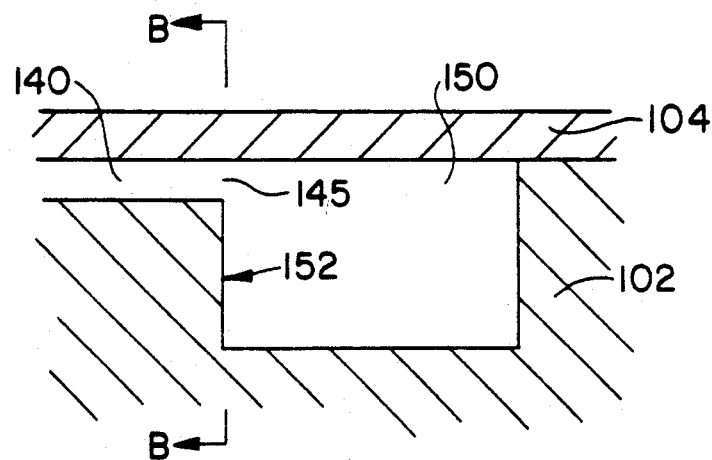
FIG. 3A is a vertical cross-section of a prior-art stop-flow junction showing a stop-flow junction formed at the junction of two separate housing members that have been welded together.
Figure 3B:
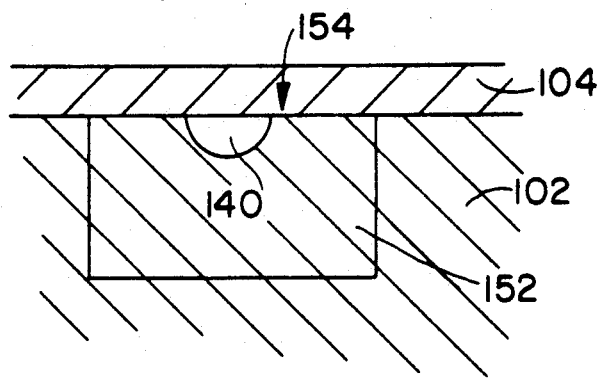
FIG. 3B is a vertical cross-section taken along line B—B of the embodiment shown in 3A.

Earlier patents have described the formation of apparatuses containing stop-flow junctions. These earlier patents and related applications have described stop-flow junctions as occurring at the junction between two body members that formed the internal cavities of the apparatus in which the junction is located. For example, FIGS. 3A and 3B show prior-art stop-flow junctions formed at an intersection between (1) a body member in which the various capillary and non-capillary chambers are formed as depressions on a surface and (2) a second body member that encloses the depressions in the surface of the first body member to form the interior chambers. In FIG. 3A, capillary channel 140 and chamber 150 are visible in body member 102, while body member 104, when sealed to body member 102, turns the depressions originally on the surface of body member 102 into internal chambers.

However, the inherent problems of sealing one body member completely to another can sometimes cause unanticipated failures of the stop-flow junction. As shown in FIG. 3B, which is a cross-sectional view taken along lines B—B of FIG. 3A, joint 154 between body members 102 and 104 intersects with the opening of capillary chamber 140 in wall 152 of chamber 150. If joint 154 is completely sealed, no problems arise. However, if during the manufacturing process, a gap is left at joint 154, capillary action will draw liquid in capillary chamber 140 into the crack and tend to defeat the purpose of stop-flow junction 145. Capillary "creep" will cause flow to occur at the edges of stop-flow junction 145, thereby allowing liquid to enter chamber 150.

Figure 4:
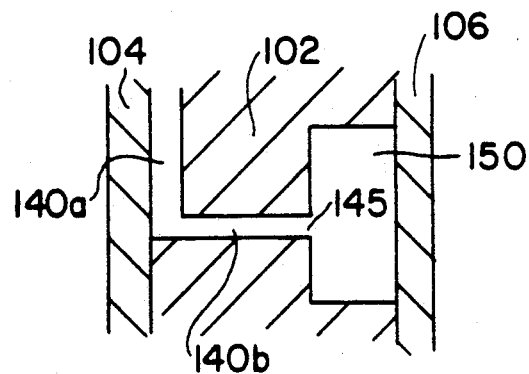
FIG. 4 is a vertical cross-section of a further embodiment of the invention showing a through-body stop-flow junction of the invention.

This potential problem can be avoided by using a through-body stop-flow junction as shown in FIG. 4. In this embodiment of the invention, measuring chamber 140 enters mixing chamber 150 not at a junction between two body members, but entirely within a single body member. As shown in FIG. 4, a diluting apparatus is made up of three body members, namely a central body member 102 that contains various depressions such as 140a and 150 that will form capillary channels and non-capillary chambers when enclosed by additional body members 104 and 106. In this case, measuring chamber 140 comprises two segments 140a and 140b. Segment 140b is formed in an injection molding process using a pin that passes through the mold used to prepare body member 102. Thus, when body members 104 and 106 are sealed to body member 102 to form the final apparatus, no joint between two or more body members exists at stop-flow junction 145, and a sharp edge is maintained around the entire perimeter of the stop-flow junction.

E. Rupture junctions as stop-flow junction protectors

Diluters that operate using stop-flow junctions of the invention can be prepared using multiple stop-flow junctions in which one of the junctions is sacrificial; i.e., it is designed to fail before other junctions in order to protect the operation of the other junctions. Such a sacrificial junction is referred to as a rupture junction in this specification.

For example, a number of preferred embodiments in which stop-flow junctions of the invention can be used contain valves that are operated by the application of an external force to the valve (see U.S. Pat. No. 5,077,017).

However, the opening and closing of valves in a diluter causes pressure waves to travel through the fluid contained in various passageways in the device. These pressure waves can cause the failure of a stop-flow junction. By providing a rupture junction designed to fail at a pressure lower than the maximum back pressure that is available at other stop-flow junctions in the same capillary passageway, relief for the pressure wave is provided in a manner that will not adversely affect the operation of the diluter or other apparatus. For example, a capillary passageway can be provided containing a valve in some portion of the passageway. If it is desirable to retain liquid in the capillary passageway on one side of the valve location, a rupture junction (i.e., a stop-flow junction with a lower maximum back pressure) can be provided on the other side of the valve in the same capillary passageway. Thus, when the valve is closed, any pressure waves will be relieved by the failure of the rupture junction prior to failure of the stop-flow junction that is designed to hold. Preferably the maximum back pressure available at the rupture junction will be at least 10% less than the back pressure available at the next weakest stop-flow junction in the passageway, more preferably at least 20% less.

Figure 5:
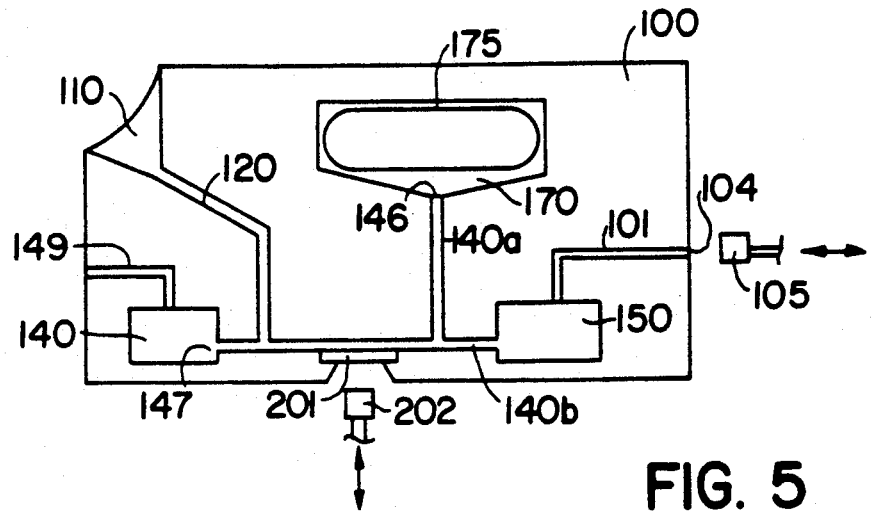
FIG. 5 is a vertical cross-section of still another embodiment of the invention showing a rupture junction in the capillary pathway that contains a stop-flow junction that is being stabilized.

Such an example is shown in FIG. 5. By now, many of the common features of this diluter will be recognized. Diluter 100 contains an application site 110, a capillary passageway 120 leading from sample application site 110 to measuring chamber 140 comprising segments 140a and 140b. Segment 140a terminates at stop-flow junction 146 where the segment meets diluent application site 170 while segment 140b terminates at stop-flow junction 145 at the entrance to chamber 150. Vent 101 and vent closing means 105 are present as in FIG. 1. A valve is present in the capillary passageway leading to measuring chamber 140, which consists of flexible wall member 201 and plunger 202, which is external to the device 100 and which operates to force flexible wall member 201 against the opposing wall to block passage of fluid. A rupture junction is present at 147 in capillary passage 120 leading to measuring chamber 140. Rupture junction 147 leads into rupture chamber 148 (for containing excess liquid) which is vented by vent channel 149.

In operation, sample applied to sample application site 110 flows through capillary channel 120 and fills all of the capillary spaces between the application site itself and stop-flow junctions 145, 146, and 147 (the last being the rupture junction). When plunger 202 is activated to close the valve, a pressure wave is generated in the capillary passageway. Since stop-flow junction (rupture junction) 147 is designed to fail before either stop-flow junction 145 or stop-flow junction 146, the pressure waves generated by closing the valve is relieved by flow of excess sample into rupture tank 148.

Although the rupture junction has been described with regard to a particular embodiment shown in FIG. 5, other embodiments will be readily apparent to those skilled in the art. Rupture junctions can be designed into any apparatus in which temporary halt of flow is desired after which events occur that are not intended to, but which may accidentally, cause flow to occur at stop-flow junctions, such as the opening and closing of various valves. By providing a location at which pressure can be relieved without adversely affecting locations where flow should still be arrested, rupture junctions provide additional stability to devices containing stop-flow junctions of the invention.

II. Integration of stop-flow junctions into a diluter

A. Components of diluter other than the stop-flow junctions

As with the apparatuses described in U.S. Pat. Nos. 4,868,129 and 5,077,017, the cartridges of the present invention includes a sample application site, a diluent application site, a measuring chamber, a mixing (receiving) chamber, various channels to provide flow of liquid between parts, and, in the case of serial diluters, a mixture isolating and measuring chamber and at least one valve controlling passage of fluid from the mixing chamber to the mixture isolating and measuring chamber. All of these parts of the cartridges have been described in the indicated applications, which can be referred to for greater detail.

The apparatus of the invention can provide for a single dilution, as in the valveless diluters described in U.S. Pat. No. 4,868,129. Serial dilutions can be provided for using a valve to control passage of a portion of the initially obtained mixture into a mixture isolating and measuring chamber. This mixture isolating chamber can take any of the forms described in U.S. Pat. No. 5,077,017. However, in preferred embodiments as described herein, the mixture isolating chamber contains essentially the same chambers and passageways as the initial diluting pathway described above. All of these parts are described in greater detail below. The following detailed description of the various parts of the apparatus is organized by following the course of action as a sample is applied to the apparatus and is diluted.

(1) Sample

The sample is a liquid and may be derived from any source, such as a physiological fluid; e.g., whole blood, blood plasma, blood serum, saliva, ocular lens fluid, cerebral spinal fluid, pus, sweat, exudate, urine, milk, or the like. The liquid sample may be subjected to prior treatment such as preparing serum or plasma from blood or dissolving or suspending a solid in a liquid. Examples of sample treatments prior to application to the apparatus of the invention include concentration, filtration, distillation, dialysis, inactivation of natural components, chromatography, and addition of reagents. In addition to physiological fluids, other liquid samples can be employed. Examples of other liquid samples include process streams, water, plant fluids, chemical reaction media, biological growth media, and the like. For the most part, the liquid will be aqueous, although other liquids can be employed. Aqueous media may contain additional miscible liquids, particularly oxygenated organic solvents, such as lower alkanols, dimethyl formamide, dimethyl sulfoxide, acetone, and the like. Usually the solvents will be present in less than about 40 vol %, more usually in less than about 20 vol %, in order to maintain the high surface tension that is present in aqueous solutions. However, the apparatus of the invention can be modified as described below for use with liquids exhibiting different surface tensions.

The apparatus as described initially herein provides for a single dilution of a sample with a diluent. Any apparatus that carries out a dilution in the manner described is considered to fall within the scope of the present invention, whether the dilution occurs by itself or as part of additional operations that occur in the device. For example, other operations can be carried out on an original sample so as to provide a mixture. This mixture is then the "sample" that is later diluted. Alternatively, provision can be made for other operations to take place on the mixture formed in the manner described above.

(2) Sample application site

The sample application site (also referred to as a sample receiving site) will generally be a cavity on a surface of the apparatus or may simply be an opening (optionally surrounded by a ring or tube) leading to the interior of the apparatus. The sample application site can contain a filter, for example, to separate red blood cells from plasma (see U.S. Pat. No. 4,753,776), or may represent a connection between the apparatus of the invention and some other apparatus that manipulates the sample prior to its entering the present dilution apparatus. For example, the application site can be a recess into which a standard capillary tube will fit.

When the sample application site is a recess for insertion of a capillary tube, the capillary tube can act either as a convenient means for transferring the sample or can act as a measuring chamber, either by completely filling the capillary or by filling the capillary to a particular mark. The sample application site in such embodiments acts as a point of transfer.

In other cases, the sample application site will be an external chamber, such as a recess on an upper surface of the device into which sample is inserted. Such surface recesses are referred to herein as external chambers, to distinguish them from chambers located in the interior of the housing that forms the cartridge. The application site can be provided with a raised lip surrounded by a catch basin so that the application site can be filled to overflowing with excess sample overflowing into the catch basin. Means for draining off a large excess of sample or sample inadvertently applied to the wrong location are discussed in U.S. Pat. Nos. 4,868,129 and 5,077,017, discussed above.

(3) Capillary passageways, including measurement chamber

When sample is applied to the sample application site, the liquid sample normally flows without the application of external force (except unassisted gravity) through a fluid passageway into a measuring chamber in the interior of the device. As described in U.S. Pat. No. 4,868,129 and U.S. Pat. No. 5,077,017, the sample can flow directly into a measuring chamber. However, it is also possible for the sample to flow into a flow directing chamber, comprising an internal chamber in the housing that forms the apparats before entering a measuring chamber, as described in U.S. Pat. No. 5,104,813. External force, e.g., from compressed air, can be used to move the sample to the measuring or flow directing chamber but is not required and in fact is not preferred. The flow directing chamber (when present) acts to divert a portion of the sample that first enters the flow directing chamber into the sample measuring chamber, which has a predetermined volume and which operates to measure and hold a portion of the sample for dilution. The remainder of the sample that enters the flow directing chamber is automatically diverted by the flow directing chamber into an exit port leading to a waste chamber or to some other means of disposing of excess sample beyond that required to fill the sample measuring chamber.

Flow directing chambers and the various appurtenances thereto, such as waste exits and waste chambers, are described in detail in U.S. Pat. No. 5,104,813 (above). However, since flow directing chambers are not used in preferred embodiments of the device containing improved flow-stop junctions of the present invention, the reader is referred to the earlier application for a complete description of this type of fluid passageway.

The measuring chamber can be a capillary channel or chamber, in which case capillary action will aid or in some cases provide all the force necessary for filling the measuring chamber with sample from the sample application site by way of the flow directing chamber. Capillary channels and chambers will generally have at least one dimension perpendicular to the flowpath in the range of 0.01 to 2.0 mm, more generally 0.1 to 1.0 mm. Capillary spaces (of whatever type) have at least one dimension at right angles to the direction of flow in the range required to support capillary flow. Capillary channels have both dimensions at right angles to the direction of flow in the range required to support flow. Capillary chambers have one dimension at right angles to flow that would not support capillary flow but provide for capillary flow by having the second dimension at right angles to flow in the required range (similar to the space between two flat plates that are closely spaced). However, larger measuring chambers that are not capillary in any dimension are also possible. The sample measuring site is said to be in "fluid receiving relationship" to the previous capillary passageways in order to indicate that unassisted flow into the measuring chamber occurs. In order for proper operation of the stop-flow junction to occur, it is essential that the measuring chamber be filed solely by capillary and gravitational forces, as will be apparent from the description of the stop-flow junction below.

It should be noted that internal spaces of a diluter that can be of either capillary or non-capillary dimensions, such as the measuring chamber, are referred to herein as "chambers" without regard to whether they are capillary channels, capillary chambers, or non-capillary chambers, in order to avoid awkward repetitive language. When the specific dimensions are important, specific language, such as "capillary chamber," is used in place of the more general "chamber." In other cases limitations on the type of space (capillary or non-capillary) that is under consideration will be apparent from the context and from the functional requirements of the space.

The geometry of the measuring chamber is such that, when diluent is added to the apparatus at a later dilution step after measurement is completed, essentially all of the sample in the measuring chamber will be expelled into the mixing chamber. One means of accomplishing this is by providing for smooth flow of diluent through the measuring chamber. A straight or curved tube with an essentially constant cross section open at both ends is thus a preferred embodiment for this type of measuring chamber. This type of measuring chamber is seen in measuring chamber 140 of FIG. 1. In preferred embodiments of this type, diluent enters the measuring chamber in a front across the entire cross-sectional area of flow. This helps avoid mixing of diluent with sample and passage of diluent through the measuring chamber without expelling essentially all of the sample, which can occur if a small stream of diluent enters into a broader cross-sectional area of the measuring chamber.

However, measuring chambers that vary in cross section are also possible, as discussed in prior applications. Nevertheless, it is desirable to have the initial portion of the measuring chamber be as small as practical, as this aids in reducing the amount of sample that may be lost from the measuring chamber when diluent initially rushes into the flow directing chamber. Initial diameters of less than 0.5 mm are desirable, preferably less than 0.2 mm. If the entrance to the sample measuring chamber is large, sample can be washed up into other passageways or chambers when diluent first enters. An unmeasured quantity of sample then flows, e.g., into a waste chamber as diluent continues to fill a flow directing chamber and then flow into both the measuring chamber and the waste chamber. Although this problem cannot be completely eliminated, using a small opening to the sample measuring chamber will reduce sample losses to acceptable levels. A small opening is therefore preferred even when the remainder of the measuring chamber is large (e.g., of non-capillary dimensions).

Additionally, while most measuring chambers will be manufactured to have a fixed volume, it is possible to provide chambers (both measuring chambers and other types of chambers and internal compartments) whose volume can be varied, for example by a closely fitting plunger used to adjust the volume of the chamber prior to use. The internal volume of such an adjustable chamber would be set to the desired value by the user, normally prior to addition of sample to the apparatus.

When sample flows into a measuring chamber, flow stops when sample reaches a stop-flow junction, as has been described in earlier applications.

(4) Diluent application site

A number of diluent application (diluent receiving) sites are disclosed in U.S. Pat. No. 4,868,129 and U.S. Pat. No. 5,077,017, discussed above. Any of these diluent application sites can be used in an apparatus of the present invention if desired. In the most preferred embodiment, the diluent application site is an internal vented chamber in the housing that forms the apparatus. Located in the chamber is a rupturable container of diluent. Glass containers are particularly preferred, although frangible plastic can also be used. An access port may be provided so that externally applied pressure can be used to rupture the container. However, it is not necessary to provide an access port, since a frangible glass or plastic container located within the housing can be broken by a sharp blow to the housing itself. If the frangible container is sized for its chamber so that deformation of the chamber walls (i.e., wall of the housing surrounding the frangible diluent container) allow the motive force of the blow to also strike the frangible container, then the frangible container will break without requiring an access hole to the chamber. This represents an improvement over prior embodiments of the diluter, as leakage of diluent from the cartridge after use is eliminated. If desired, a flexible area can be provided on the wall of the chamber surrounding the diluent container, such as by providing a thin housing in a target region at that location. Providing a thinner and more flexible housing will increase the possible deformation upon receipt of a blow. The central point of the target region can be thicker than the surrounding flexible region in order to better absorb the energy of the blow without breaking.

Exact dimensions are best determined emperically for a given diluent container, chamber, and housing material. As an example, an ABS housing with a wall thickness of 0.020 inch, a target region thickness of 0.015 inch, and an ampule chamber 0.275 inch thick containing glass ampules ranging in thickness from 0.258 to 0.272 inch, worked well.

A passageway connects the diluent chamber to the flow directing chamber or measuring chamber. Diluent flows into the measuring chamber so that the hydrostatic pressure at the stop-flow junction is exceeded and the sample is expelled into the receiving chamber along with a portion of the diluent. Excess diluent flows into a waste chamber in some embodiments or remains in the diluent application chamber and/or flow directing chamber.

(5) Mixing chamber

There are no particular restraints on the geometry of the receiving (mixing) chamber other than that smooth fluid flow be provided for in order to prevent trapping of gas bubbles. Providing entry of sample and diluent into a lower portion of the receiving chamber and providing an upper surface of the receiving chamber that slopes upward toward a vent both aid in avoiding trapped bubbles. It is desirable, however, to ensure that the exit for mixed diluent and sample (if present in the receiving chamber; see below) is located at a distance from the entrance for sample and diluent. If the exit and entrance are located too close to each other, diluent flowing into the chamber while mixture is exiting can reach the exit too early and result in diluent rather than mixture reaching the second measuring chamber. Other provisions can be made to ensure smooth flow of mixture through the exit, such as locating the mixture exit at a low location and the diluent entrance at a high location for diluents that are less dense than the mixture of sample and diluent (and vice versa).

(6) Vents

The vents used in the various chambers of the device can merely be a small hole terminated by a stop-flow junction in order to avoid exit of liquid from the device or can be a more sophisticated vent designed for gas exit without exit of liquid (e.g., a microporous, hydrophobic plug capable of passing air but not hydrophilic liquids). Stop-flow junctions can also be placed in the early portion of a long vent to prevent a relatively large quantity of liquid from entering the vent from the vented chamber. A vent or other means to allow exit of trapped air is provided at every location in the apparatus in which the trapping of air would interfere with the passage of liquids between the various chambers and/or channels of the device. If desired vents can be selectively opened and closed, as described for vent-assisted stop-flow junctions.

A preferred manner of forming vents is to use interior waste space in the housing as vent space to catch any liquids that may accidently be forced through a vent channel. The initial venting channel leading from, for example, a mixing chamber to the waste space is then essentially an internal venting space, with an external vent at a location in the waste space that is unlikely to be reached by liquid which can function as the final external vent. In preferred embodiments, this internal-/external venting system can also provide the surge tank arrangement already discussed for vent-assisted stop-flow junctions, in addition to providing the additional safety function of trapping potentially dangerous samples or reagents inside the housing (which can be disposable).

(7) Size of chambers and capillaries

Although there is no theoretical upper limit on the size of samples that can be measured and diluted in this first step (or later steps) using an apparatus of the invention, the method and apparatus are particularly suitable for measuring and diluting small quantities of liquids. Accordingly, the sample measuring chamber will generally have a volume of from 0.1 $\mu L$ to 10 $\mu L$, preferably 1 $\mu L$ to 30 $\mu L$, and most preferably 3 $\mu L$ to 10 $\mu L$. The receiving chamber, which acts to limit diluent volume and fix the ratio of sample to diluent, generally has a volume of from 3 µL to 1000 µL, preferably 10 µL to 300 µL, and most preferably 30 µL to 200 µL, thereby providing dilution ratios of from $10^4:1$ to 3:1, preferably $10^3:1$ to 4:1, and most preferably 100:1 to 5:1. Channels through which capillary flow will take place will usually have opposing walls spaced in the range of about 0.01 mm to 2 mm, more usually about 0.1 mm to 1 mm. The capillary spaces can be tubular (which does not necessarily imply a circular crosssection but can be square or other regular shapes) or can represent the spaced formed by flat plates and side walls with the side walls being spaced further apart than a capillary distance. A tubular chamber with at least one flat side (e.g., a square cross-sectional area, a rectangle with adjacent sides differing in length by no more than a factor of 1:2 to 1:4, or a semicircular chamber) are preferred for ease of manufacture in cases where channels are being formed by the joining of two adjacent surfaces, one of which can be flat.

It should be recognized that statements in this specification indicating upper and lower limits of ranges are to be taken as individually designating a series of upper limits and a series of lower limits which can be utilized in any combination. For example, a typical upper limit and a preferred lower limit may be used in combination to define a range of intermediate preference.

(8) Valves

Any type of valve that will control the passage of liquids between chambers and/or channels can be used in the apparatus of the present invention. Simple valves that can be actuated to move between an open and a closed position by the application and release of a simple external force are preferred.

Examples of such valves include resilient blocking members that are present in or adjacent to a liquid flowpath. For example, a resilient blocking member can be present in a converging or diverging pathway so that the narrow portion of the pathway is blocked by the resilient blocking member when the blocking member is in its normal position. Application of force in a direction generally away from the restricted portion of the flowpath and toward the wider portion of the flowpath will open the valve by moving the blocking member away from the narrow walls of the flowpath. Alternatively, a normally open valve can be provided which is blocked by movement of a resilient blocking member to a location that cuts off flow of liquid. Specific examples of such valves are set forth in more detail below.

Other examples of such valves include sliding pins closely engaging a channel that laterally traverses a fluid flowpath. The pin has a segment capable of obstructing flow through the flowpath when the pin is in a first position and a segment capable of allowing flow through the flowpath when the pin is in a second position. Examples of such pins include rectangular pins having a flowpath channel between two opposite faces of the pin, the flowpath channel being out of register when the block is in a closed position and in register with the principal flowpath when the block valve is open. Pins with circular cross-sections can be used by providing an obstructing segment of the pin that snugly engages the channel in which the pin fits and obstructs the flowpath when the pin is in a closed position. A smaller cross-sectional area (such as is present in the handle of a dumbbell) provides an annular flowpath around the smaller, central portion of the pin when the pin valve is in the open position.

A resilient member can be provided to bias the pin into either the closed or the open position. A force acting on the pin can then slide the pin to a second location so that the pin valve is in the alternate position.

In preferred embodiments, access for the application of an external force on the pin is provided so that the pin can be moved between its two positions. For example, a section of the pin that protrudes externally from the apparatus can be provided so that a force acting parallel to the sliding axis of the pin can move the pin from its first biased position to a second position by acting against the direction of the biasing force. Alternatively, an aperture leading from a face of the pin opposite the biasing force to the external environment can be provided. Externally applied pressure, such as from compressed air or a finger of an external apparatus that enters the aperture, can be used to slide the pin between its open and closed positions.

A resilient seal can be provided to prevent loss of liquid through the aperture while allowing force to be applied to the pin. Such seals can also be provided for the resilient blocking members described above.

The valves that can be used as integral parts of a cartridge of the present invention are not limited to those specifically exemplified here. Rather, any valve can be used that can control the flow of liquids through small flowpaths, such as flexible walls (e.g., latex) of a flowpath that can be compressed to restrict flow of liquid through the flowpath. Additionally, a dissolvable barrier can be provided in instances where an initially closed valve will be opened once and then maintained in the open position.

It is also possible to provide an external valve. For example, a flowpath through which capillary flow occurs can be blocked by closing an external vent. When the external vent is closed, liquid cannot enter the capillary pathway because of air or other gases in the capillary pathway. Opening the vent allows liquid to enter the capillary pathway. If the vent is closed while liquid is contained in the capillary pathway, the isolated liquid can later be used for other manipulations.

Valves consisting of external vent controls can be used in any situation where flow occurs through a capillary pathway (so that trapped air is effective to control flow of liquids) and where no free liquid that might leak is stored in the cartridge prior to use. Encapsulated liquid (e.g., in glass ampules) can be present in devices using external vent controls. In many cases it is desirable to store pre-measured diluents (which can contain reagents) in the cartridge when the cartridge is delivered to an end user. Internal mechanical valves or rupturable barriers are preferred for such uses in order to prevent accidental leakage.

By providing valves that can be operated by a simple externally applied force, a cartridge-like device can be provided in which the valves are opened and closed in a predetermined manner by an analytical device into which the cartridge is inserted. This analytical device can contain various optical and/or other types of sensors for detecting the presence of liquids or analytes in various mixing and/or measuring chambers of the cartridge in addition to providing means for opening and closing the valves and is therefore sometimes referred to in this specification as a monitor.

(9) Reagents and assays

The apparatus of the present invention can be designed for use with a particular assay or can be designed and prepared as an apparatus in which multiple assays can be carried out, depending on the order in which various valves are opened and closed and the contents of the various diluents, which can contain reagents for the development of a detectable signal (e.g., a color reaction) that depends on the presence of an analyte in the sample.

Reagents can be provided at various locations in the device. Incubation times can be controlled by either manual operation of valves or by a mechanically or electronically stored program in the monitor into which the cartridge is inserted. The program would control the order and timing of opening and closing valves. The programmed device would contain solenoids or other means for providing force to open and/or close valves or rupture containers containing diluent. In embodiments in which flow through a capillary pathway is being controlled by the opening and closing of a vent, a movable sealing pad that is capable of closing the vent will form part of the external programmed device into which the cartridge is inserted.

(10) Monitor

The apparatus shown in the Figures and otherwise described herein will normally be inserted into an apparatus in which analytical measurements on the sample can made. The analytical instrument is sometimes referred to as a monitor. Optical measurements are common and are the preferred type of measurement for use in monitors. A light source and a detector are located in the monitor so that the light impinges on the desired location in the mixing and dilution chamber, passes through the chamber and the material enclosed therein, and impinges on the detector located at the other side of the cartridge. This is accomplished by inserting the cartridge into a chamber of the monitor so that all of the parts are placed into proper registration with each other. The present invention requires nothing new in the way of light sources, detectors, and registration means, since all spectrophotometers that engage cuvettes and carry out light measurements there through provide the necessary detection and registration systems.

However, the monitor can provide additional light sources and detectors to detect the presence of the fluid at various points in the fluid pathways throughout the cartridge. In this specification such components are called system control components since they represent a means by which the monitor can verify whether sample, the diluted mixture, or the like have reached the proper points in the fluid pathway in the proper sequence and at the proper time. For example, light sources and detectors can be placed at opposite sides of the cartridge so that the detector measures light passing through the sample in passageway 120 at optical window 122 to determine when sample has been applied to the cartridge (see FIG. 6). Various operations of the cartridge can be automatically provided by detecting presence of absence of various liquids in the cartridge, as has been described in previously listed applications and patents.

The monitor is generally designed to be capable of detecting correct operation of the cartridge by providing sensors that detect the presence of liquids at numerous locations in the fluid pathways of the cartridge and comparing the signals provided by the sensors with the signals that would be produced during proper operation of the cartridge. Automatic detection of proper operation is desirable when the cartridge is in the hands of an unskilled user, which is a desired end use of the cartridge. For example, if the user must apply a drop of blood (as the sample) to the sample application site, several problems can occur. Some patients have trouble obtaining a drop of blood of sufficient volume. For example, if proper operation of the cartridge requires 25 $\mu l$ of blood and only 20 $\mu L$ is added to the sample application site, the sample measuring site may not completely fill. If diluent is then added automatically (such as after a preselected time), the dilution will be greater than desired, and an incorrect result will be obtained.

(11) Construction

The cartridges of the invention are typically prepared from molded plastic as described in U.S. Pat. No. 4,756,844, the only principal differences between the production methods described in the patent and the production required for the present apparatus being in the mold used to form the various chambers. As indicated in the patent, plasma etching can be used to improve flow characteristics through the various capillary pathways, since most molding plastics are hydrophobic and need to be rendered hydrophilic for reproducible capillary flow to occur.

(12) Second stage of diluter

In particular, the present inventors contemplate providing serial dilution and mixing capabilities using a mixture measuring and isolating chamber hydrostatically connected to the mixing chamber and a valve controlling passage of fluids from the mixing chamber to the mixture isolating chamber. The first dilution takes place as indicated above during which time the valve is closed to prevent escape of liquid from the mixing chamber. After the first mixture is formed, the valve controlling flow to the mixture isolating and measuring chamber is opened, and fluid flows from the mixing chamber under the influence of hydrostatic pressure and/or capillary attraction. The portion of the mixture isolating chamber into which the mixture flows is smaller in volume than the total volume of mixed sample and diluent. This volume is determined by the geometry of the chamber, the amount of hydrostatic pressure available from liquid in the mixing chamber, and any capillary forces that are present. U.S. Pat. No. 5,077,017, described above, describes various geometries that can be provided for a mixture isolating chamber depending on whether the intent is to carry out a second dilution in the original mixing chamber of to transport the isolated portion of the mixed sample and diluent to another location for further dilution and/or analysis. Any apparatus that carries out a single dilution as described above and a second dilution as described in the prior application will fall within the scope of the present invention.

However, a particularly preferred embodiment of the present invention is directed to an apparatus in which serial dilutions are carried out, both of which fall within the scope of the single-dilution invention set forth above. In such embodiments, the mixture isolating chamber will comprise the same types of chambers and passageways as described previously, with the exception that they will operate on the mixture as a sample rather than on an initially obtained sample.

B. Specific example of apparatus

(1) Description of exemplary apparatus

A series of Figures is provided to illustrate a particularly preferred embodiment of the invention. The embodiments shown in the Figures are not intended to be comprehensive, and numerous other embodiments within the scope of the appended claims will be apparent to those of ordinary skill in the field of the invention.

Figure 7A:
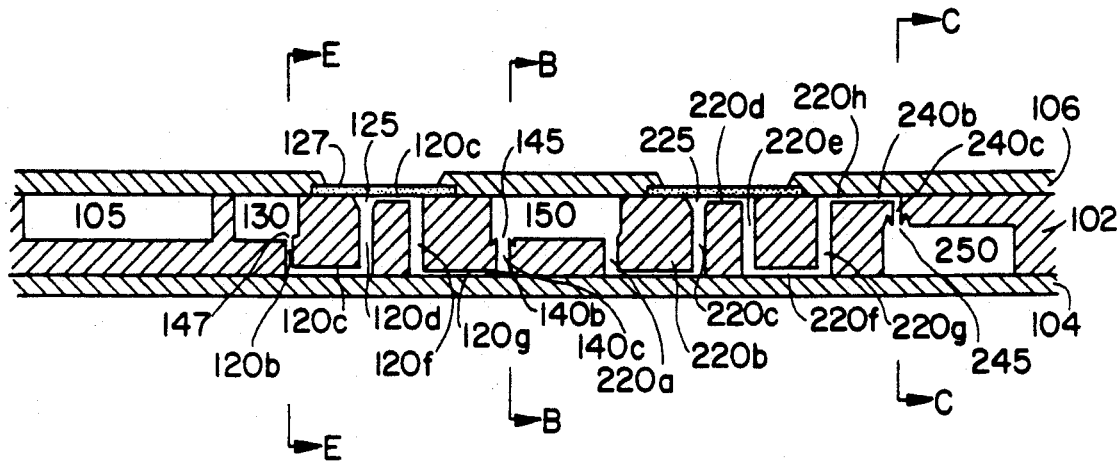
FIGS. 7A through 7J are a series of vertical cross-sections of the embodiment of FIG. 6 taken at locations A—A through J—J of the embodiment FIG. 6.
Figure 7B:
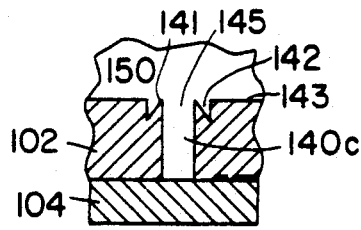
Figure 7C:
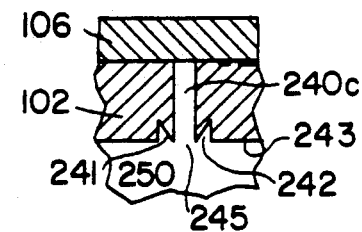
Figure 7D:
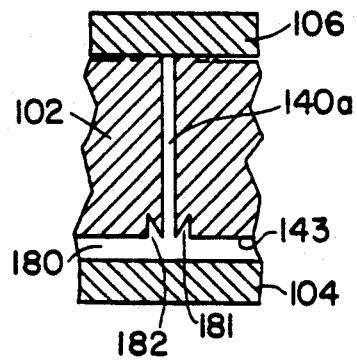

FIG. 6 is a plan view from the front of a first embodiment of the invention in which lines A—A, D—D, etc., show the location of the corresponding cross-sectional views shown in FIGS. 7A, 7D, etc. As shown in FIG. 7A, housing 100 is prepared from three separate pieces, a central base member 102 and two cover plates 104 and 106. Chambers formed in the front face of base member 102 are shown with solid lines in FIG. 6. Passageways formed in the back face of base member 102 are shown by dashed lines in FIG. 6. Through connections, which are generally holes passing from one face to the other, are shown by circles in FIG. 6. All such passageways would be visible in embodiments prepared from transparent plastic, as described in U.S. Pat. No. 4,756,844. However it is also possible to prepare the cartridge from an opaque material if provisions are made for light paths at the appropriate locations.

The apparatus shown in FIG. 6 is capable of carrying out two dilutions serially. Parts of the apparatus associated with the first dilution are numbered from 110 to 182. Parts of the apparatus associated with the second dilution are numbered from 205 to 282. Where two parts perform the same function in the first and second dilutions, the last two digits of the identifying number are the same. Parts of the apparatus associated with the housing are numbered from 100–106. The apparatus will be described by reference to the indicated numbers while following a sample through a series of two dilutions in the apparatus.

A sample is added initially to sample application site 110. The sample flows down capillary passageway 120 to measuring chamber 140. Passageway 120 consists of an initial segment 120a connecting diluent application site 110 to the remainder of the passageway, a segment 120b (leading to a rupture junction 147 shown in FIG. 7I), and a segment 120c containing valve 125 that is connected at one end to both segment 120a and 120b and at the other end to measuring chamber 140. Segment 120b terminates in rupture chamber 130, which has a venting exit 132 and venting channel 133 leading to internal vent 134.

Sample continues to flow into and fill measuring chamber 140, which is of capillary dimensions. Measuring chamber 140 consists of vertical segment 140a terminating at stop-flow junction 146 and horizontal segments 140b and 140c (the latter terminating at stop-flow junction 145 as shown in FIG. 7B). Sample flow stops when the leading edge of the sample reaches the various stop-flow junctions 145–147. Vent channel 152, located in a upper portion of dilution and mixing chamber 150, is connected to vent surge tank 154 and eventually to vent opening 156 by channel 153 to allow controlled exit of gases from chamber 150.

Frangible container 175 is (not visible in this view) provided in an internal chamber 170 that functions as the diluent application site. Chamber 170 is connected by internal passageway 180 to measuring chamber 140 at stop-flow junction 146. Passageway 180 is vented to atmosphere via a vent channel 182 leading to an internal vent 182.

Mixing in chamber 150 can be provided by a number of techniques, such as are described in U.S. Pat. No. 5,028,142. It is possible to begin mixing the sample and diluent as they enter the chamber so that any mixture entering the vent will have approximately the same composition as the mixture remaining in the chamber. Better is to allow undisturbed filling of the chamber. In either event, the volume of the vent is sufficiently small so that negligible error results. Additionally, it is possible to include a separate stop-flow junction in the vent channel to prevent excess exit of liquid, should higher accuracy be desired. Such a stop-flow junction in the vent channel exiting the mixing chamber is shown below in FIG. 7G.

Exit 210 in receiving chamber 150 serves as the entrance for mixture into the second dilution portion of the apparatus. During the first dilution, however, passageway 220 is blocked by valve 225, and trapped air prevents mixture from entering the passageway. When the valve is open, a portion of the mixture flows through exit 210 and channel 220 to a second measurement chamber 240, referred to herein as the mixture measurement chamber, which, as for measurement chamber 140, consists of a vertical segment 240a and horizontal segments 240b and 240c. Mixture measurement chamber 240 terminates at stop-flow junction 245 where chamber 240 intersects with mixture diluting chamber 250 and at stop-flow junction 246 at the diluent end of the measurement chamber.

Second diluent is provided in rupturable diluent container 275 (not visible in this view) contained in diluent chamber 270. Diluent becomes available at diluent application site 270 upon rupture of the container, flows into channel 280, and enters mixture measurement chamber 240 at stop-flow junction 246. Channel 280 is vented at vent 282. As with the first dilution, the hydrostatic pressure provided by the diluent is available to overcome the back pressure at stop-flow junction 245. Diluent flows through mixture measuring chamber 240 into mixture receiver chamber 250, expelling trapped air through vent exit 252 and channel 253 leading to surge chamber 254. Surge chamber 254 is provided to give the volume necessary for proper operation, as described above. Mixing takes place in mixing chamber 250 in the same manner as in mixing chamber 150.

FIGS. 7A through 7J show a series of cross-sectional views at different locations of the embodiment shown in FIG. 6. As mentioned previously, the apparatus is assembled by attaching cover plates 104 and 106 to central body member 102 in which the various chambers and passageways are formed. In FIGS. 7A-7H, the top sides of the figure represents the back face of the embodiment shown in FIG. 6 and the bottom side represents the front face except when indicated otherwise.

FIG. 7A is a sectional view of the embodiment shown in FIG. 6 taken along lines A—A, with the back of the embodiment of FIG. 6 appearing at the top of FIG. 7A. The three body members that make up housing 100 are visible in this figure. A central body member 102 has various depressions in its upper and lower surfaces (as viewed) along with through passageways from one surface to the other. Front (104) and back (106) face plates are sealed to the central body member 102 to form the internal cavities that make up the capillary and non-capillary chambers and passages of the diluter.

Turning to the internal cavities on the left side of the figure and moving toward the right, cavity 105 plays no part in the operation of the diluter but is an internal cavity that prevents the central body member 102 from being unduly thick, thereby reducing time spent during molding operations. Rupture tank 130 is next visible along with segment 120b of capillary passageway 120 and the rupture junction 147 at the intersection of passageway 120c and chamber 130. Passageway segment 120b is visible along the front face of body member 102. Initial segment 120a of passageway 120 (not visible in this view; see FIG. 6) joins the remainder of the passageway at the common junction between segments 120b and 120c.

The use of passageways on both faces of central body member 102 and through passages between faces to prepare capillary passageways can be seen in section 120c, 120d, 120e, 120f, and 120g of capillary passageway 120, along with valve 125. Segment 120c is formed by a depression in the front face of body member 102 that is covered by face plate 106. Sebment 120d is a through passage between segment 120c and the depression that forms the loction of valve 125. Valve 125 operates by application of external pressure to flexible covering 127, which blocks passage of fluid when forced into depression 125. Depression 125 is connected to depression 120e in the back face of central body member 102, and from there to through passageway 120f that connects to the last segment of passageway 120, a depression 120g in the front face of body member 102.

Segment 120g is connected to horizontal measuring segment 140b at a location about midway between through passageway 120f and through passageway 140c, which terminates at stop-flow junction 145 in mixing chamber 150. Vertical measuring segment 140a (not visible in this view; see FIG. 6) also is connected to segment 120g and segment 140b at their common junction.

Passageway 220, which leads from mixing chamber 150 to measuring chamber 240, consists of segments 220a-220h and valve depression 225. These passageway segments function in essentially the same manner as the various segments of passageway 120. Measuring chamber 240a (not visible; see FIG. 6) and 240b both join with the far end of segment 220h. Measuring segment 240b leads to through passageway 240c, which terminates in stop-flow junction 245 at the entrance to chamber 250.

FIGS. 7B through 7H are expanded sectional views of different stop-flow junctions of the diluter embodiment of FIGS. 6 and 7A. FIG. 7B, taken along line B—B of FIG. 7B, is capillary stop-flow junction 145 in chamber 150. Through passageway 140c terminates in nozzle 141 located in a recessed area 142 of wall 143 of chamber 150. FIG. 7C, taken along line C—C of FIG. 7A, shows capillary stop-flow junction 245 in chamber 250. Through passageway 240c terminates in nozzle 241 located in recess 242 of wall 243 of chamber 250.

Figure 7E:
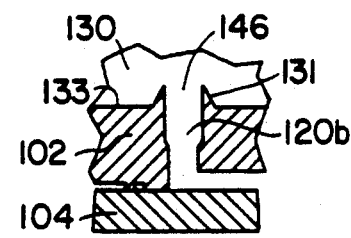

A typical upper stop-flow junction is shown in FIG. 7D, taken along line D—D of FIG. 6. Through passageway 140a terminates in nozzle 181 located in recess 182 of wall 183 of chamber 180. FIG. 7E, taken along line E—E of FIG. 7A, shows rupture junction 146 in rupture chamber 130. Through passageway 120b terminates in nozzle 131 located in wall 133 of chamber 130.

Use of different diameters to provide different maximum back pressure can be seen from a comparison of FIGS. 7D, 7B, and 7E, which respectively show an upper capillary stop-flow junction 146 that is designed never to break, a lower capillary stop-flow junction 145 that is designed to hold initially and then break when diluent is applied, and a rupture junction 147 that is designed to break before either of the other two. The scale drawings show a small diameter for upper stop-flow junction 147 (FIG. 7D), an intermediate diameter for lower stop-flow junction 145 (7B), and a large diameter for rupture junction 146 (7E).

Figure 7F:
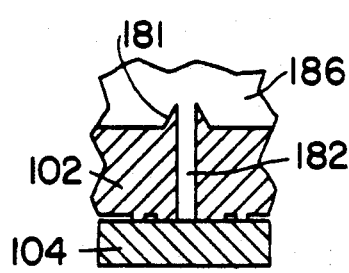
Figure 7G:
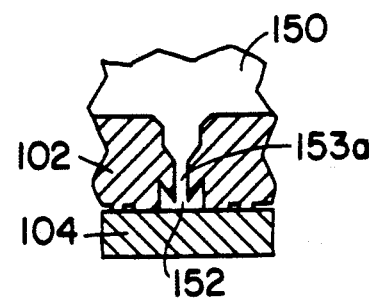
Figure 7H:
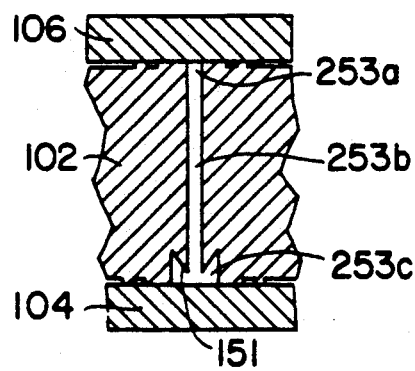

Stop-flow junctions of the invention are also present at other locations. FIG. 7F, taken along line F—F of FIG. 6, shows vent 182 terminating in an interior waste space 186. A nozzle 181 is present to increase back pressure. FIG. 7G, taken along line G—G of FIG. 6, shows a stop-flow junction 152 in the initial through passageway 153a of vent channel 153 at the exit of mixing chamber 150. A similar stop-flow junction 252 is present in vent channel 253 at the exit of mixing chamber 250 (not shown in detail; see FIG. 6). These two stop-flow junctions act to reduce the amount of liquid that exits the mixing chambers, thereby providing for more accurate dilution and mixing steps. Additional stop-flow junctions can be provided at locations in vent channels more distant from the mixing (or other liquid-containing) chamber for additional leakage protection, such as at through passageway 256 of vent channel 253. FIG. 7H, taken along line H—H of FIG. 6, shows this through passageway in detail. Through passageway 253b traverses body member 102 from the initial portion 253a of vent channel 253 on the back face of body member 102 to the later portion 253c on the front face. A stop-flow nozzle 251 is visible at the location where passageway 253b enters channel 253c.

Figure 7I:
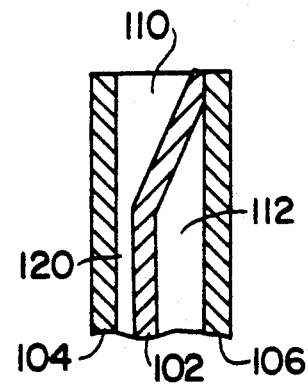
Figure 7J:
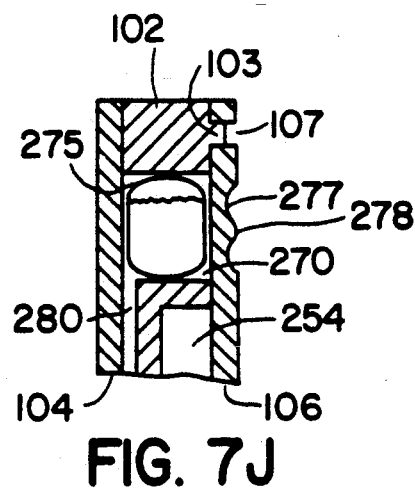

Several construction features of the diluter are seen in FIGS. 7I and 7J. FIG. 7I is a sectional view of the sample application site 110 taken along line I—I of FIG. 6 showing sample application cavity 110 and an initial section of capillary passageway 120 along with interior waste chamber 112. FIG. 7J is a sectional view of the diluent application chamber 270 taken along line J—J of FIG. 6 showing diluent application site (chamber) 270, an initial portion of diluent channel 280, and a portion of surge tank 254. Diluent container 275 is visible in chamber 270. A pin 103 in body member 102 that fits into a hole 107 of body member 106 in order to insure proper registration of body members 102 and 106 during manufacture is also visible. A flexible target region 277 with a a thicker central target point 278, which is struck by an external blow in order to break container 275, is also visible in this view.

The entire apparatus shown in FIGS. 6 and 7 would be approximately 5 cm high and less than 8 cm wide with body member 102 being about 0.7 cm in thickness. The cartridge can readily be prepared in other sizes to carry out other analytical measurements.

(2) Operation of exemplary serial diluter

Outlined below is a typical cartridge operating sequence with reference to the embodiment shown in FIGS. 6 and 7:

(1) A sample of unknown volume is applied to the sample application site 110.

(2) As sample flows into the cartridge through passageway 120, it is detected through the sample detection window 122 using a light source and detector located in the monitor in which the cartridge is located (not shown).

(3) Sample continues to flow into the cartridge, filing passageway 120 to the rupture junction at 147. The sample does not break the rupture junction 147 or flow into rupture tank 130, since rupture tank vent 134 is closed (by the monitor).

(4) Sample continues to flow into the cartridge through passageway 120 and through control valve 125.

(5) Sample continues to flow into the cartridge and passageway 120, entering the measuring chamber at a junction between vertical segment 140a and horizontal segment 140b. Sample moves through vertical segment 140a to upper stop-flow junction 146 and through horizontal segments 140b and 140c to lower stop-flow junction 145. Sample does not break lower stop-flow junction at 145 and flow into the dilution and mixing chamber 150 since valve 225 is closed and mixing chamber surge tank 154 is not vented to atmosphere (i.e., valve 225 and vent 156 were previously closed by the monitor).

(6) Shortly after sample is detected at upper stop-flow junction 146, rupture tank vent 134 is opened to atmosphere by the monitor.

(7) As soon as rupture tank vent 134 is opened to atmosphere, control valve 125 is closed by the monitor. Since rupture junction 147 is designed to provide the least resistance to flow along the sample flow path, any shock that is created by closing control valve 125 is dissipated by sample flowing into rupture tank 130. This maintains the position of the sample at upper stop-flow junction 146 and lower stop-flow junction 145. By closing control valve 125, the portion of sample filling the capillary passageway at segments 140a, 140b, and 140c is isolated from the rest of the sample, which will remain in the various parts of passageway 120 during remaining operations, including the portion of passageway 120 to the right of valve 125 but to the left of the junction of passageways 140a and 140b. The isolated portion in measuring chamber 140 is a precise portion of the original sample.

(8) At this point, dilution and mixing chamber 150, the vent channel 153, and the mixing chamber surge tank 154 are opened to atmosphere by the monitor opening vent 156.

(9) Next, diluent ampule 175 is broken by a blow on target point 278 (provided by the monitor), and diluent flows through the diluent application site 170 into channel 180 and fills channel 180 to and including vent 182.

(10) Once diluent fills the diluent application site 170 and adjoining spaces, the additional hydrostatic pressure transmitted through sample in measuring chambers 140a, 140b, and 140c on the lower stop-flow junction 145 causes flow of diluent and the sample isolated in the measuring chamber 140 into mixing chamber 150. An initial segment 153a of channel 153 leading to stop-flow junction 152 is also filled by the diluted mixture.

(11) Once mixing chamber 150 has been completely filled, a mixing ball (not shown) in chamber 150 is reciprocated, mixing the diluent and sample, thereby completing the first dilution sequence.

(12) To begin the second dilution, control valve 225 is opened by the monitor, allowing a portion of the mixture from mixing chamber 150 to flow into the rest of the cartridge.

(13) Sample (i.e., the first mixture) flows through passageway 220 and valve 225 and into the upper arm 240a and lower arms 240b and 240c of the mixture measuring passageway 240. Flow stops at upper stop-flow junction 246 and lower stop-flow junction 245. Sample does not break lower stop-flow junction 245 and flow into the the second mixing chamber (250) since vent 256 is closed by the monitor and surge tank 254 is not vented to atmosphere.

(14) Shortly after sample is detected by the monitor at upper stop-flow junction 245, control valve 225 is closed. By closing this valve the portion of diluted sample (from the first dilution) filling measuring segments 240a, 240b, and 240c is isolated from the rest of the sample. The isolated portion is a precise portion of the mixture from dilution and mixing chamber 150.

(15) At this point, mixing chamber 250, vent channel 253, and surge tank 254 are opened to atmosphere by opening vent 256.

(16) Next, the diluent ampule 275 is broken, and diluent flows through diluent application site 270 and diluent channel 280, filling these chambers to vent 282.

(17) Once diluent fills diluent channel 280, additional hydrostatic pressure on lower stop-flow junction 245 causes diluent and the sample in segments 240a and 240b of the measuring chamber to flow into second mixing chamber 250, vent 252, and the portion of vent channel 253 below stop-flow junction 255.

(18) Once second mixing chamber 250 has been completely filled, a mixing ball (not shown) is reciprocated, mixing the diluent and sample and completing the dilution sequence.

(3) Chemical processes occurring in the diluter

Figure 8:
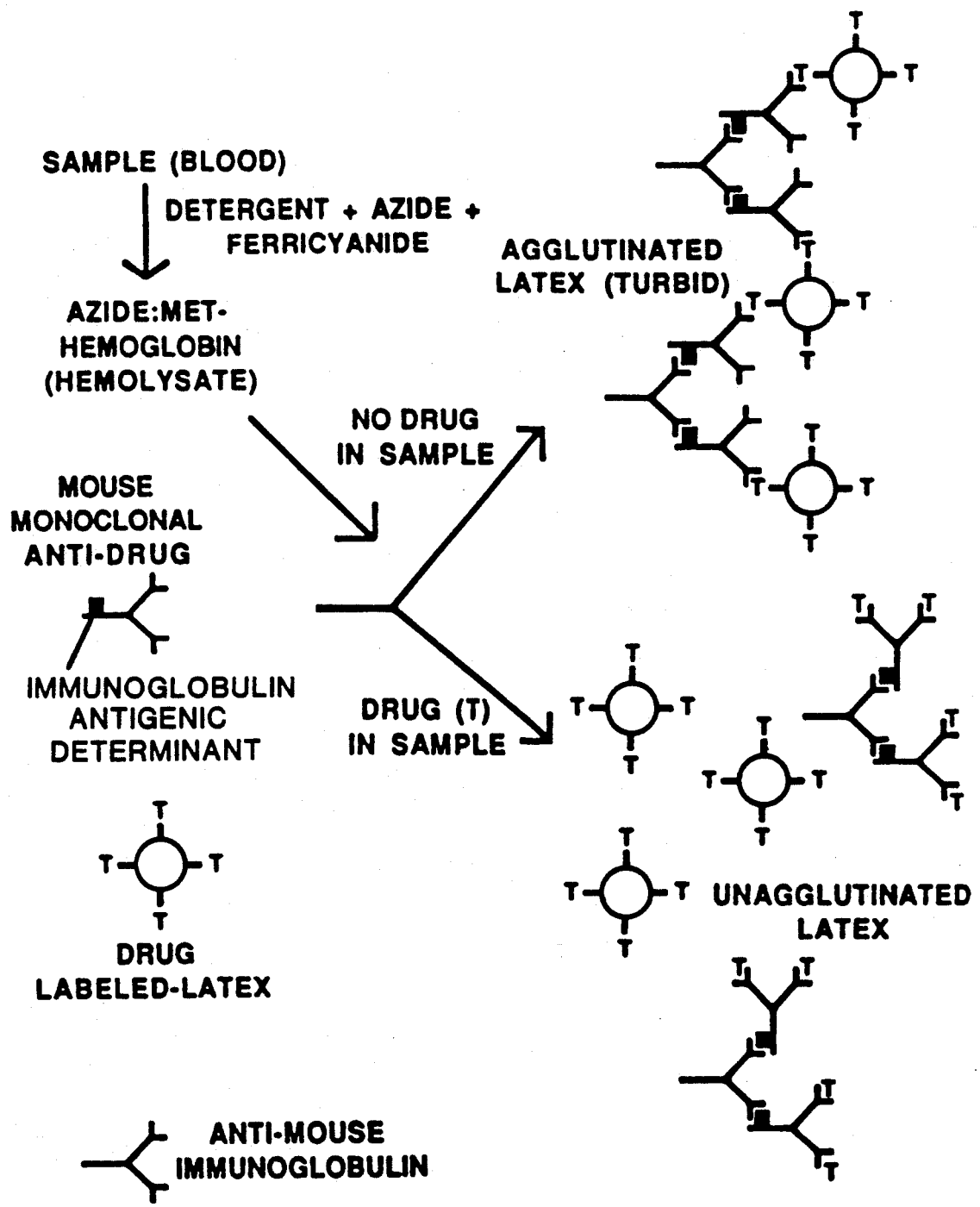
FIG. 8 in a schematic diagram of chemistry associated with a specific analysis that can be carried out in the embodiment of FIGS. 6 and 7.

FIG. 8 is a schematic diagram showing reagents that could be used with a cartridge of the type as shown in FIGS. 6 and 7 to carry out a specific diagnosis. A therapeutic drug, such as theophylline, is assayed turbidimetrically in the cartridge by a latex-agglutination-inhibition method. The assay uses whole blood as the sample. To convert the sample to a form suitable for the assay, red cells and other "formed elements" are dissolved by dilution into a medium containing detergent. The assay system (monitor and reagent-containing cartridge) accomplishes this dissolution by a combined dilution/mixing step (the first dilution) and then performs a second dilution/mixing operation to combine diluted sample with two initially dry reagents that are dissolved and resuspended by mechanical mixing. One of the reagents is a dispersion of latex particles which agglutinate at a rate inversely related to drug concentration in the sample. The assay reaction is measured by following the increase of turbidity in the reaction medium over about 20 seconds.

A sample from an unmeasured blood drop will be applied to sample application site 110. Sample will flow into measuring chamber 140 through passageway 120. When container 175 is broken, a detergent solution, which also contains excess ferricyanide and azide, will flow through measuring chamber 140 into mixing chamber 150, pushing the blood sample ahead of itself. The mixture of blood and first reagent/diluent solution will fill mixing chamber 150. Homogeneous mixing of blood and the first diluent will now occur, driven by a reciprocating mixer. Ferricyanide converts the hemoglobin to its met form, which complexes with azide to give a well-defined spectral complex. The hemoglobin concentration of the sample is then calculated by measuring the absorbance of the diluted blood at 560 nm. The plasma concentration of drug can then be calculated from the concentration in the blood hemolysate from a simple mathematical relationship, no matter what the original sample hematocrit was.

The valve in channel 220 will then be opened to allow a portion of the mixture to flow into the measurement (mixture isolation) chamber system. Once the mixture measuring chamber 240 has been filled, diluent container 275 is broken, allowing a glycine buffer diluent to flow into the dry antibody-latex reagent chamber 250, resuspending the reagent (which is coated on the chamber walls of chamber 250), after displacing the sample of denatured blood (i.e., the isolated mixture) from mixture measurement chamber 240 into the mixing/reaction chamber 250. Two dry reagents are present at different locations in chamber 250. Reagent 1 contains drug-labelled latex particles and anti-mouse immunoglobulin ("second antibody"). Reagent 2 contains mouse monoclonal antibody to drug. The denatured blood/reagent mixture will then be mixed and assayed for theophylline by measurement of the change in turbidity over about 20 seconds. In absence of drug in the sample, the anti-drug binds to the drug-labeled latex particles. This is not enough to cause rapid agglutination of the latex. The second antibody binds to the anti-drug both free in solution and bound to the latex, thereby agglutinating the particles. Drug in the sample competes with drug bound to latex for anti-drug antibody and thus inhibits the agglutination reaction. The assay is set up so that over the clinically relevant range of drug, the agglutination reaction is almost fully inhibited.

The proper operation of a diluter using stop-flow junctions of the invention has been demonstrated using this chemistry. Other assays, such as those described in U.S. Pat. No. 5,104,816, can also be used in the diluter as described above.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a device combination which comprises an electronic instrument and an analytical cartridge adapted to removably fit into said instrument for carrying out an analytical assay, wherein said cartridge comprises a housing containing a capillary stop-flow junction located at a junction where a capillary passageway used to transport a liquid in said housing enters a non-capillary internal chamber in said housing, an improvement which comprises:
   means for selectively trapping gas in said capillary passageway and non-capillary chamber, whereby when said means for trapping is activated and said liquid enters said capillary passageway, said gas is compressed by said liquid as said liquid flows through said capillary channel and said liquid stops flowing at said stop-flow junction, wherein said means for selectively trapping gas comprises an vent opening in said housing, a vent passageway connecting said chamber to atmosphere surrounding said cartridge at said vent, and a sealing member located externally to said housing which is capable of selectively closing said vent opening, wherein said sealing member is located in and operated by said electronic instrument.

2. The device combination of claim 1, wherein said vent passageway comprises a capillary passageway and a non-capillary vent-surge chamber.

3. The device combination of claim 1, wherein said sealing member comprises a flexible pad that reversibly contacts said vent opening.

4. The device combination of claim 1, wherein internal pressure of said compressed gas balances head pressure of said sample at said stop-flow junction when sample has stopped flowing at said junction.

5. A vent-assisted capillary stop-flow junction comprising a housing surrounded by a gaseous atmosphere and an electronic instrument into which said housing removably fits, wherein (1) said housing comprising:
   a. an internal chamber;
   b. liquid receiving means for accepting a liquid;
   c. a capillary channel connecting said liquid receiving means to said chamber; and
   d. a channel leading out of said chamber and connecting said chamber to the atmosphere and surrounding said housing;
   (2) said electronic instrument comprises means for selectively closing said channel and sealing said chamber from the atmosphere;
wherein when (1) said means for selectively closing is activated and gas is trapped in said capillary passageway and said chamber and (2) said liquid is concurrently applied to said means for accepting a liquid, said liquid flows through said capillary channel, compresses air trapped in said housing by said means for trapping, and stops flowing at said stop-flow junction.

6. The vent-assisted capillary stop-flow junction of claim 5 wherein said vent passageway comprises a capillary passageway and a non-capillary vent-surge chamber.

7. The vent-assisted capillary stop-flow junction of claim 5 wherein said sealing member comprises a flexible pad that reversibly contacts said vent opening.

8. The vent-assisted capillary stop-flow junction of claim 5, wherein internal pressure of said compressed gas balances head pressure of said sample at said stop-flow junction when sample has stopped flowing at said junction.

9. A method for increasing stability of a capillary stop-flow junction in a housing surrounded by a gaseous atmosphere, which comprises the steps of: (1) providing a housing having:
   i. an internal chamber of non-capillary dimensions;
   ii. liquid receiving means for accepting a liquid;
   iii. a capillary channel connecting said sample receiving means to said chamber;
   iv. said stop-flow junction at the intersection of said capillary channel and said chamber; and
   v. a venting channel leading out of said chamber and connecting said chamber to the atmosphere surrounding said housing;
(2) inserting said housing into a device having means for selectively closing said venting channel and sealing said chamber from the atmosphere; and
   (3) closing said venting channel prior to applying said liquid to said means for accepting a liquid, whereby said liquid flows through said capillary channel and stops flowing at said stop-flow junction.

10. The method of claim 9, wherein said venting channel has a volume selected so that compression of air trapped in said capillary channel, said chamber, and said venting channel produces an internal pressure that opposes flow of said liquid that is no greater than hydrostatic pressure acting in the direction of said flow.

* * * * *